United States Patent [19]
Haenggi

[11] Patent Number: 5,413,575
[45] Date of Patent: May 9, 1995

[54] MULTIFUNCTION ELECTROCAUTERY TOOL

[75] Inventor: Thomas J. Haenggi, Long Beach, Calif.

[73] Assignee: Innovative Medical Technologies, Ltd., Long Beach, Calif.

[21] Appl. No.: 229,693

[22] Filed: Apr. 19, 1994

[51] Int. Cl.⁶ .............................. A61B 17/39
[52] U.S. Cl. ...................... 606/45; 604/35; 606/39
[58] Field of Search ............ 606/42, 45, 39, 40, 606/41, 49, 50, 52, 29; 604/902, 35

[56] References Cited

U.S. PATENT DOCUMENTS

| | | | |
|---|---|---|---|
| 4,487,600 | 12/1984 | Brownlie et al. | 604/35 |
| 4,562,838 | 1/1986 | Walker | 606/45 X |
| 5,242,442 | 9/1993 | Hirschfeld | 606/45 X |
| 5,246,440 | 9/1993 | Van Noord | 606/45 |
| 5,269,781 | 12/1993 | Hewell, III | 606/45 |
| 5,318,565 | 6/1994 | Kuriloff et al. | 606/45 X |

*Primary Examiner*—Peter A. Aschenbrenner
*Attorney, Agent, or Firm*—Roy A. Ekstrand

[57] ABSTRACT

A multifunction electrocautery tool includes an elongated housing within which a generally cylindrical suction tube is slidably supported. A slide control is mechanically coupled to the suction tube and movable to control the retraction and extension thereof. The slide control includes an aperture coupled to the suction passage of the suction tube to facilitate a single finger or thumb control of the suction tube position and suctioning action. A cauterizing and cutting blade is supported proximate the suction tube and is coupled to a source of RF electrical energy by a connecting wire. In one embodiment, electrical controls for the cauterizing blade are supported upon the upper surface of the elongated housing while a pair of oppositely positioned slide controls are provided on right hand and left hand side surfaces to facilitate either right or left hand operation. In an alternate embodiment, a slide control is supported upon the upper surface which includes a control aperture coupled to the suction passage of the suction tube.

22 Claims, 6 Drawing Sheets

FIG. 2

MULTIFUNCTION ELECTROCAUTERY TOOL

FIELD OF THE INVENTION

This invention relates generally to surgical implements and particularly to electrocautery tools having associated suction apparatus.

BACKGROUND OF THE INVENTION

In many surgical procedures, various blood vessels of tissue within the operating area are routinely coagulated during the surgical procedure by application of a high frequency electrical current. This technique is widely used and is usually carried forward by applying one electrical circuit connection to the patient's body and applying an additional electrical circuit connection to a conductive cauterizing probe or element. The electrical connections are coupled to a source of high frequency electrical energy through appropriate switching apparatus with the result that high frequency electrical current flows the probe into and through the patient's body when the probe is energized. The energy of the high frequency electrical current coagulates the blood vessels at the point of contact thereby sealing off blood flow. Despite the presence of coagulation equipment in most surgical procedures, a quantity of blood is found within the operative area which is typically removed by a suction device.

While virtually any shaped electrocautery device will provide coagulation, it has been found advantageous in many surgical procedures to utilize a blade-like probe sufficiently sharpened for incision and cutting while maintaining its conductive properties to be utilized as an electrocautery probe. The result is a surgical tool which is capable of cutting and cauterizing tissue during the surgical procedure.

In most surgical environments, it is highly desirable if not essential to avoid or at least minimize wasted moves and manipulation of instruments during surgical procedures. Thus, time spent by surgeons and their assistants in switching between operations of cutting, cauterizing and suctioning a surgical area should be avoided to the extent possible.

In attempting to meet the demanding needs of modern surgical procedures and efficiency, practitioners in the art have provided a variety of combination tools which combine one or more implements in a common tool package which provide capability for cutting, cauterizing and suctioning a surgical area. For example, U.S. Pat. No. 3,906,955 issued to Roberts sets forth a SURGICAL CAUTERIZING TOOL having suction means in which an elongated generally cylindrical housing supports a movable or extendable suction tube in proximity to a cauterizing blade. A slide button is movably supported upon the generally cylindrical housing and is coupled to the suction tube facilitating the retraction and extension of the suction tube relative to the cauterizing blade. In its anticipated use, a source of RF electrical energy is coupled to the cauterizing blade through a foot operated switch while a vacuum source is coupled to the suction tube.

U.S. Pat. No. 5,035,695 issued to Weber, Jr. et al. sets forth an EXTENDABLE ELECTROCAUTERY SURGICAL APPARATUS AND METHOD in which an elongated housing supports a generally cylindrical suction tube together with a slidably supported electrocautery blade movable with respect to the extended suction tube. A slide member is movably supported upon the housing of the tool and is coupled to the electrocautery blade to facilitate extension and retraction of the blade with respect to the extended end of the suction tube.

U.S. Pat. No. 4,170,234 issued to Graham sets forth a SYSTEM FOR USE WITH ELECTRO-SURGICAL PENCIL having an elongated generally cylindrical housing supporting a replaceable electrocautery blade and a plurality of parallelly spaced electrical connections to a source of RF electrical energy. A rocker switch element includes a plurality of metal contacts to provide electrical switching between the plurality of electrical connections and the electrocautery blade to vary the electrical energy applied to the blade.

U.S. Pat. No. 4,307,720 issued to Weber, Jr. sets forth an ELECTROCAUTERY APPARATUS AND METHOD AND MEANS FOR CLEANING THE SAME in which an elongated generally cylindrical housing supports a retractable electrocautery blade coupled to a movable slide switch. A suction passage is formed in the housing and is coupled to a vacuum source. A guide is supported upon the housing and closely spaced to the electrocautery blade to provide a cleaning and scraping action as the blade is drawn into the housing through the guide.

U.S. Pat. No. 4,427,006 issued to Nottke sets forth ELECTROSURGICAL INSTRUMENT for providing an interface between an electrosurgical electrode and an electrosurgical generator. A hollow handle supports an electrode at one end and receives a three-wire cable through the opening in the other end. The wires of the cable are supported and positioned on a substantially flat insert which has three contact pins in electrical connection with the connectors. A conductor plate overlies the insert and is equipped with conductor strips for interconnecting the conductive pins.

U.S. Pat. No. 4,112,950 issued to Pike sets forth MEDICAL ELECTRONIC APPARATUS AND COMPONENTS. The apparatus includes a high frequency, high voltage generator, a therapeutic instrument, a compound electrical power and control cable connected therebetween and a switch for selectively connecting at least one signal current conductor in the cable to the instrument.

U.S. Pat. No. 3,828,780 issued to Morrison, Jr. sets forth a COMBINED ELECTROCOAGULATOR-SUCTION INSTRUMENT having an elongated body of electrically nonconductive material supporting a hollow generally cylindrical combination suction and cauterizing unit at one thereof. The remaining end of the instrument is coupled to source of electrical energy and vacuum to provide cauterizing and suction.

U.S. Pat. No. 15,195,959 issued to Smith sets forth an ELECTROSURGICAL DEVICE WITH SUCTION AND IRRIGATION which provides a disposable electrosurgical device which is useful in performing laparoscopic surgical procedures. The device includes both suction and irrigation capabilities in which the application of electrical current, the application of suction and the transmission of irrigation fluid to the surgical site can be conveniently regulated through control mechanisms contained within the surgical handpiece.

Thus, the prior art exemplifies past invention having certain superficial similarities to the present invention in that all have electrosurgery capabilities and some provide means for electrosurgery and fluid transfer. Unfortunately, all possess inherent limitations from an ergonomics and manufacturing engineering standpoint.

These limitations include, for example, the fact that the valves for suction or irrigation incorporate complex pistons and compression methods to conduct conduit collapsing which is complex, costly, and limits of performance due to kinking and clogging reliability due to complex springs and pistons. Additionally, many of the prior art utilize control of fluids from remote proximation in relation to the hand piece as an attached stop clock valve is used, being attached to its proximal end for fluid control, requiring major relocation of both hands required. Of the systems that utilize vent control of suction by a bleed hole, the bleed holes are normally located at twelve o'clock and only include foot control activation and activation of cut and cautery functions impeding precise activation of the electrosurgery current and causing fatigue for the surgeon's foot. Consequently, of the systems that provide bleed hole or control valve at any location, offer no method to control over the retraction deployment of a vacuum tube. Others utilize a suction regulation by means of an occluder taking two individuals to operate and is cumbersome. With the different instruments provided with retraction of blade or tube, there is no means to control over the retraction of the tube or blade and fluid control from the same module and location at one convenient step. There is no design that permits a suction control module built in the same element that additional controls over the deployment of the retraction, in addition to one convenient step.

While the foregoing devices have provided some measure of success in combining various functions of electrosurgical tools, they tend to be impractical or subject to substantial difficulty when manipulated by surgeons in the demanding environment of a surgical procedure. There remains, therefore, a continuing need in the art for evermore improved, easy to use, convenient and efficient multifunction electrocautery tools.

SUMMARY OF THE INVENTION

Accordingly, it is a general object of the present invention to provide an improved multifunction electrocautery tool. It is a more particular object of the present invention to provide an improved multifunction electrocautery tool which combines the functions of cutting, coagulating and suctioning in a single, easily handled and easily controlled instrument. It is a still more particular object of the present invention to provide an improved multifunction electrocautery tool which while combining the functions of cutting, coagulating and suctioning in a single surgical instrument, further accommodates the operative control of the suctioning and coagulating functions without resort to additional controls such as foot operating controls or the like.

In accordance with the present invention, there is provided a multifunction electrocautery tool comprises: an elongated housing; an elongated suction tube slidably supported within the housing and defining a suction passage therethrough; a slide control coupled to the suction tube and movably supported upon the housing, the slide control defining a control aperture and a control passage coupling the aperture to the interior passage of the suction tube; and an electrocautery blade supported upon the housing, the slide control being operable to move the suction tube within the housing and the control aperture being used to alter the suction characteristic of the suction tube.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawings, in the several figures of which like reference numerals identify like elements and in which:

DESCRIPTION OF THE PREFERRED EMBODIMENTS

Figures 1, 13:
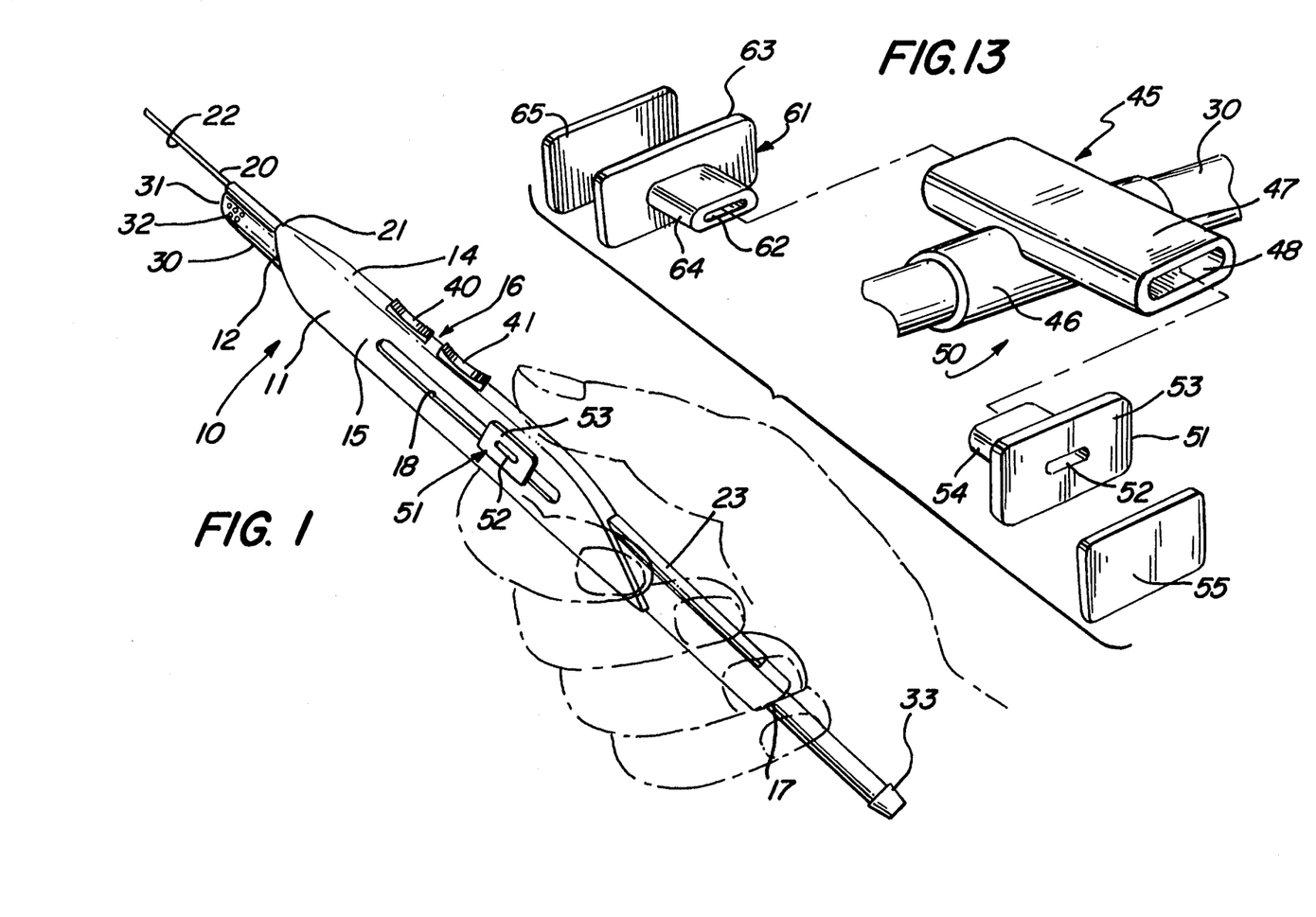
FIG. 1 sets forth a perspective view of an improved multifunction electrocautery tool held in a typical aspirating position.
FIG. 13 sets forth a perspective assembly view of the aspiration control slider of the present invention multifunction electrocautery tool.

FIG. 1 sets forth a perspective view of a multifunction electrocautery tool constructed in accordance with the present invention and generally referenced by numeral 10. Electrocautery tool 10 includes an elongated housing 11 defining end portions 12 and 17, an upper surface 14, and side surfaces 15 and 16 (the latter better seen in FIG. 3). Housing 11 further defines a pair of elongated slots 18 and 19 formed in side surfaces 15 and 16 respectively. Housing 11 further supports a blade receptacle 21 which in turn receives a replaceable electrocautery blade 20. Blade 20 defines a cutting edge 22 and is fabricated of a conductive metal. A connecting wire 23 is received within end portion 17 of housing 11 and is coupled to a conventional source of radio frequency or RF electrical energy (not shown). In the manner set forth below in FIG. 5, connecting wire 23 is electrically coupled to blade 20 through blade receptacle 21.

Tool 10 further includes an elongated generally cylindrical suction tube 30 having an end 31 defining a plurality of apertures 32 positioned proximate blade receptacle 21 and a connecting end 33 configured to be coupled to a conventional vacuum source (not shown). As is set forth below in FIG. 5 in greater detail, suction tube 30 is slidably supported within housing 11 such that end 31 is positionable in the retracted position shown in FIG. 1 or, alternatively, extendable outwardly to the position shown in FIG. 3.

Figure 3:
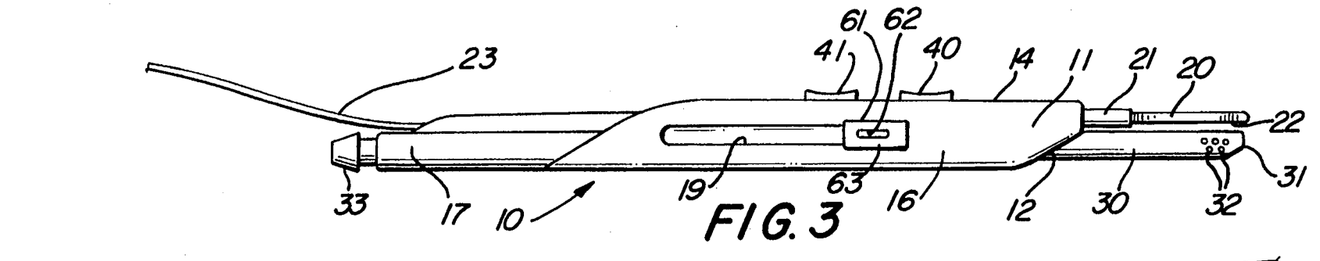
FIG. 3 sets forth a side elevation view of the present invention multifunction electrocautery tool.

In accordance with an important aspect of the present invention, an aspiration control generally referenced by numeral 50 and shown in detail in FIG. 13 is supported within housing 11 and includes a pair of slide control buttons 51 and 61 (the latter seen in FIG. 3). In further accordance with an important aspect of the present invention, slide control buttons 51 and 61 are movable upon side surfaces 15 and 16 respectively of housing 11 and are coupled to suction tube 30 by a fitting 45 (seen in FIG. 13). Thus, slide control buttons 51 and 61 are mechanically coupled to suction tube 30 such that movement of slide control buttons 51 and 61 forwardly and rearwardly within slots 18 and 19 respectively produces a corresponding movement of suction tube 30. In the position shown in FIG. 1, suction tube 30 is substantially retracted and thus slide control buttons 51 and 61 are positioned substantially rearward within slots 18 and 19. Thus, in the position shown in FIG. 1, suction tube 30 is substantially retracted exposing electrocautery blade 20 in a typical cutting and cauterizing configuration.

Figure 2:
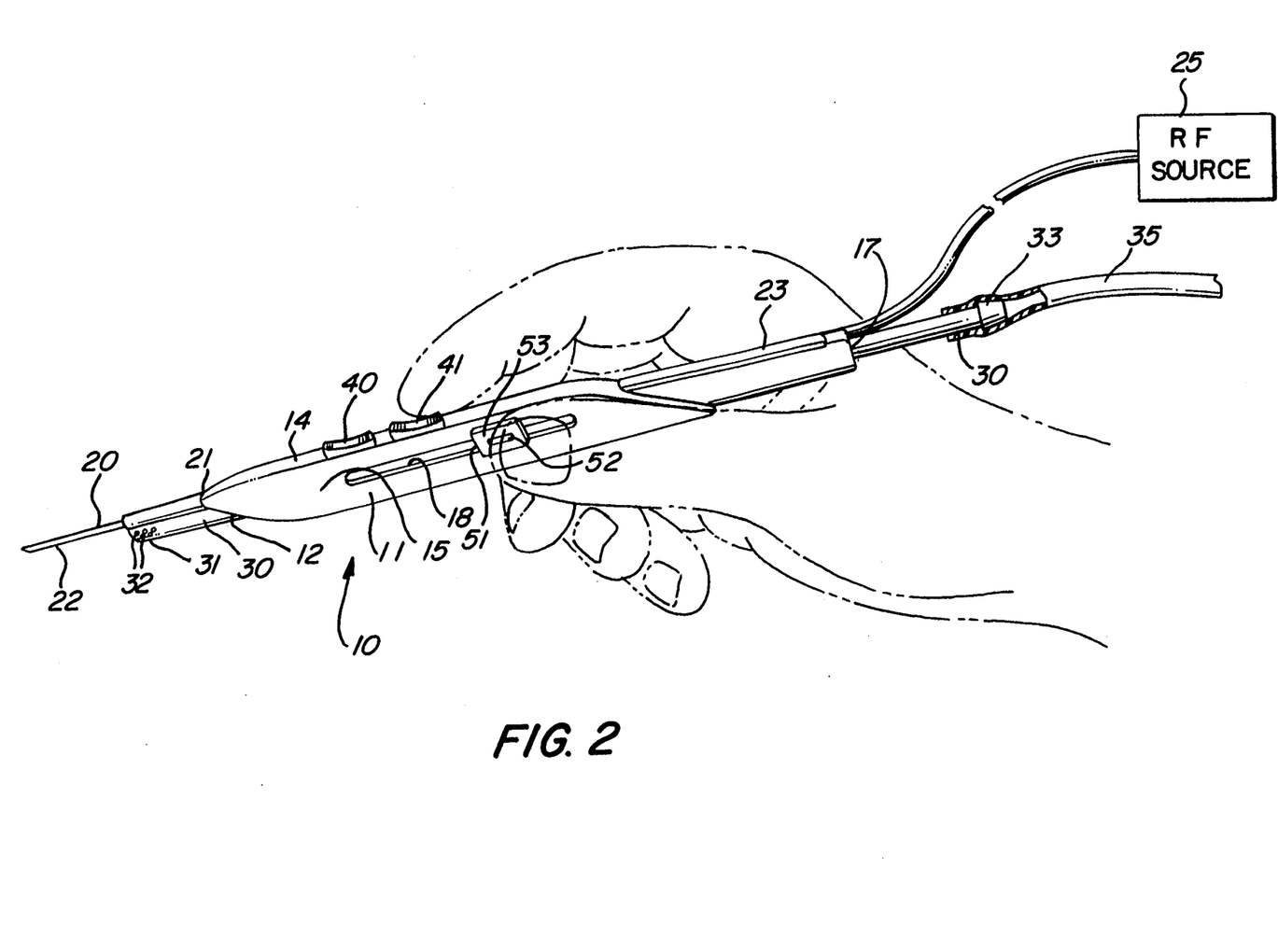
FIG. 2 sets forth a perspective view of an improved multifunction electrocautery tool constructed in accordance with the present invention held in an typical hand position utilizing cutting, cauterizing and evacuating of the surgical site.

In accordance with a further important aspect of the present invention, slide control buttons 51 and 61 define outwardly facing finger surfaces 53 and 63 respectively which facilitate engagement of slide control buttons 51 and 61 with the user's thumb in the manner shown in FIG. 2 to control the position of suction tube 30. In addition, slide control buttons 51 and 61 define respective control apertures 52 and 62 respectively which are coupled to interior passage 34 of suction tube 30 (seen in FIG. 7). Thus, control apertures 52 and 62 communicate with the vacuum applied to suction tube 30 via connecting end 33 in the anticipated use of the present invention electrocautery tool. As is set forth below in greater detail and in accordance with an important aspect of the present invention, the use of redundant slide control buttons 51 and 61 on each side of housing 11 enables electrocautery tool 10 to be configured for convenient use by both right-handed and left-handed users. In the configuration shown in FIG. 1, tool 10 is configured for use by a right-handed person grasping tool 10 in the right hand. Accordingly, a sealing membrane 65 (seen in FIG. 13) is applied to slide control button 61 to block control aperture 62. Correspondingly, membrane 55 (also seen in FIG. 13) is removed from finger surface 53 of slide control button 51 exposing control aperture 52. As a result and as is better seen in FIG. 2, the user is able to control the suction effect of suction tube 30 by alternatively covering or exposing control aperture 52 with the application of the user's thumb to finger surface 53. This novel system for controlling the suction of the suction tube is extremely convenient in use in that the user normally utilizes a thumb to move slide control button 51 and thereby position suction tube 30. Thus, little or no additional motion is required to either increase or decrease the suction at end 31 of suction tube 30. As a result, the user is able to control the amount of suction entirely with one hand without resorting to cumbersome additional controls utilized in the prior art.

Figures 4, 5:
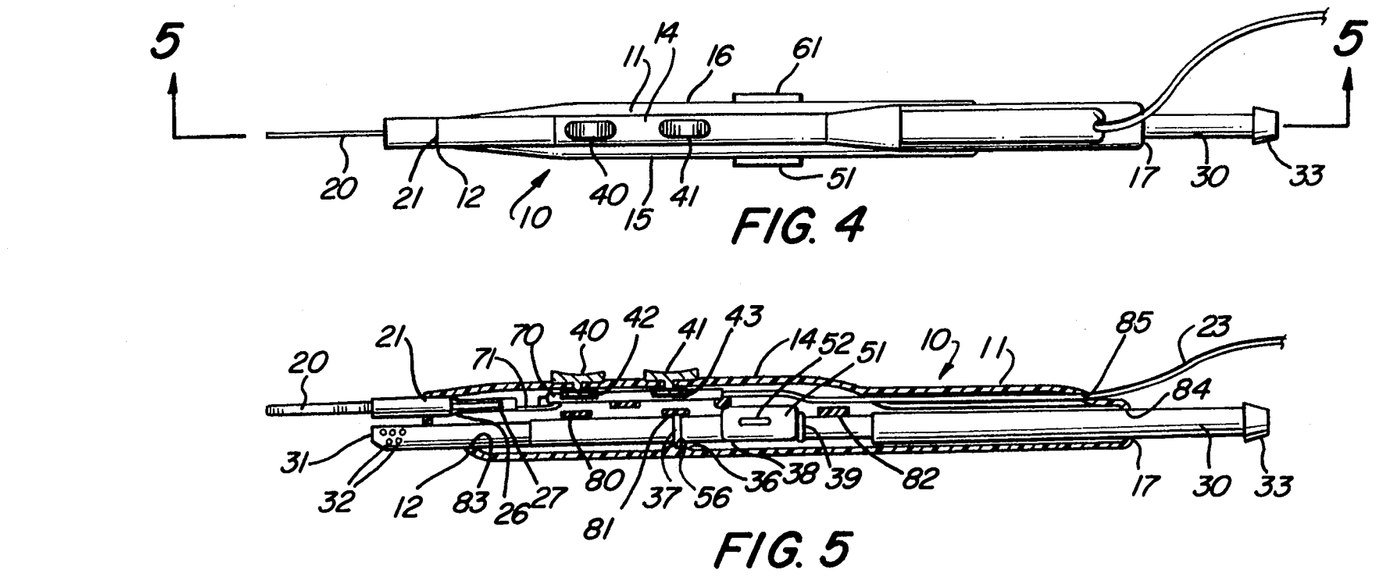
FIG. 4 sets forth a top view of the present invention multifunction electrocautery tool.
FIG. 5 sets forth a section view of the present invention multifunction electrocautery tool taken along section lines 5—5 in FIG. 4.

Tool 10 further includes a pair of switch buttons 40 and 41 supported upon upper surface 14 which as is better seen in FIG. 5 are operable to control a pair of depressible switches 42 and 43 are used in controlling the RF electrical energy applied to blade 20.

FIG. 2 sets forth a perspective view of the present invention multifunction electrocautery tool held by a user's hand in a typical grip which facilitates the multifunction use of the present invention tool for cutting, cauterizing and suctioning a surgical wound or site. As described above, tool 10 includes a housing 11 having ends 12 and 17, a top surface 14 and side surfaces 15 and 16. As is also described above, tool 10 further includes a blade receptacle 21 supporting a cauterizing blade 20 having a cutting edge 22 in a removable attachment. Tool 10 further includes a slidably supported suction tube having an end 31 defining apertures 32 and a connecting end 33 facilitating connection to a conventional vacuum source.. An electrical connecting wire 23 extends through housing 11 and is coupled to blade receptacle 21 under the control of a pair of switch buttons 40 and 41 supported upon upper surface 14. In the position shown in FIG. 2, it is assumed that a right hand user is manipulating tool 10 and thus in accordance with an important aspect of the present invention, slide control button 61 supported upon side 16 of housing 11 and shown in FIG. 3 is covered by a seal membrane 65 (seen in FIG. 3). Correspondingly, to facilitate the control of suction action applied to suction tube 30, slide control button 51 slidably supported within slot 18 and coupled to suction tube 30 has seal membrane 55 (seen in FIG. 13) removed from finger surface 53 to expose control aperture 52. In the anticipated use of tool 10, connecting wire 23 is coupled to a conventional source of RF electrical energy 25. Energy source 25 should be understood to be constructed entirely in accordance with conventional fabrication techniques. Similarly, and in further accordance with the anticipated use of the present invention electrocautery tool, connecting end 33 of suction tube 30 is coupled to a conventional vacuum source (not shown) by a conventional coupling apparatus such as a hollow flexible plastic tube 35.

In operation, with the user grasping tool 10 in the manner shown, the user is able to manipulate slide control button 51 forwardly and rearwardly within slot 18 to control the extension of end 31 of suction tube 30 and thus position suction tube 30 in either the retracted position shown in FIG. 2 exposing electrocautery blade 20 or to extend end 31 of suction tube 30 to the position shown in FIG. 3. As is set forth below in FIGS. 6A through 6C and FIG. 5, the position of suction tube 30 is continuously adjustable throughout the entire range of movement of slide control button 51 within slot 18 and is detentably positioned at a plurality of fixed referenced positions for the user's convenience. The detent positioning of suction tube 30 is particularly advantageous in permitting the suction tube position to be held fixed at a given detent position of extension without the continued involvement of the user's thumb. In accordance with an important aspect of the present invention providing substantial economy of motion and ease of use, the user is able to control the suction applied to end 31 of suction tube 30 by simply adjusting the user's thumb position upon surface 53 of slide control button 51 to either completely or partially cover control aperture 52 or, alternatively, to remove the user's thumb therefrom and entirely expose control aperture 52. As described above, control aperture 52 communicates with the interior passage or suction passage of suction tube 30 and, as a result, functions as a "bleed hole" which when left uncovered substantially reduces the vacuum or suction applied to end 31 of suction tube 30. Correspondingly, with control aperture 52 partially blocked, the vacuum or suction at end 31 of suction tube 30 is correspondingly increased and is maximized when the user completely blocks control aperture 52. Thus, through the easy manipulation of the user's thumb upon a single slide control button, the user is able to readily adjust both the extension and degree of suction of suction tube 30. The advantage of this single manipulation control cannot be overemphasized in the demanding surgical art in which each motion and each delicate manipulation of the surgeon's hand is critical to the maximum opportunity for success in the surgical procedure.

Concurrent to the user's manipulation of suction tube 30 and the degree of suction therein using slide control button 51 and control aperture 52, the user is able to also control the RF electrical energy applied to electrocautery blade 20. As can be seen in FIG. 2 with the user grasping tool 10 in the manner shown such that the user's thumb is able to manipulate slide control button 51, the user's index finger quite naturally is aligned with upper surface 14 and is able to conveniently manipulate switch buttons 40 and 41 to control the electrical energy applied to blade 20. Thus, with no further adjustment of hand position, the user is able to press either of switch buttons 40 and 41 to provide convenient electrical energy control thereby controlling cauterizing actions of blade 20. Once again, it must be emphasized that the single hand position use of the present invention electrocautery tool facilitated by the advantageous positioning of switches 40 and 41 together with slide control button 51 provides a single multifunction electrocautery tool which facilitates the complete control of cutting, cauterizing and suctioning of a surgical wound without readjustment of the user's hand position in grasping the tool. As a result, the present invention structure provides advantages not realized in the prior art devices which tend to be cumbersome and difficult to manipulate in their attempts to provide multifunction electrocautery tools.

It will be apparent to those skilled in the art that the use of tool 10 when configured in the manner shown in FIG. 3 exposing slide control button 61 and control aperture 62 is essentially the reverse of that shown in FIGS. 1 and 2 to accommodate left-handed use of the present invention tool. Correspondingly, membrane 55 is placed upon finger surface 53 of slide control button 51 to provide closure of control aperture 52 in accordance with such left hand use. The position of switch buttons 40 and 41 upon upper surface 14 is equally appropriate for both left and right hand users and thus provides further advantage of the present invention electrocautery tool. In all other respects apart from the removal of membrane 65 and the application of membrane 55, the use of the present invention electrocautery tool in a left hand fashion is the same as that described above for right hand use in FIGS. 1 and 2.

With specific reference to FIG. 3 in which a side view of tool 10 is set forth and in which suction tube 30 is shown in the extended position, tool 10 is configured for left hand use. As described above, tool 10 includes an elongated housing 11 defining ends 12 and 17 and supporting a blade receptacle 21 within which an electrocautery blade 20 having an edge 22 is removably supported. Tool 10 further includes an elongated generally cylindrical suction tube 30 having an end 31 defining a plurality of apertures 32 and a connecting end 33. Housing 11 defines an upper surface 14, a side surface 16 and an elongated slot 19. A connecting wire 23 extends into end 17 of housing 11 and is operatively coupled to blade receptacle 21 under the control of switch buttons 40 and 41.

Figure 6A:
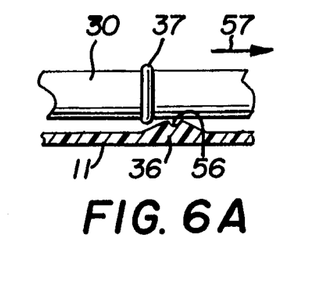
FIGS. 6A through 6C set forth sequential partial section views of the suction tube detent mechanism of the present invention multifunction electrocautery tool.
Figure 6B:
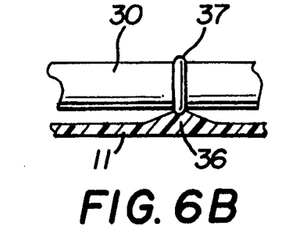
Figure 6C:
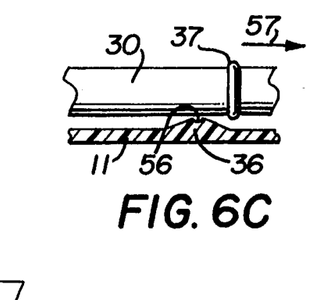

In operation, in the position shown in FIG. 3, slide control button 61 is moved forwardly within slot 19 to extend suction tube 30 forwardly placing end 31 at its maximally extended position. Thus, the position shown in FIG. 3 facilitates the suctioning of the surgical wound at end 31 under the control of the user by alternatively exposing control aperture 62 or partially or completely covering aperture 62. It should be noted that end 31 of suction tube 30 defines a plurality of apertures 32 which facilitate the attachment of a blade cleaning accessory shown in FIGS. 7 through 9. In addition, apertures 32 provide alternative suction flow paths in the event end 31 is obstructed by tissue within the surgical wound site. As described above, the configuration of tool 10 in FIG. 3 is utilized in accommodating left hand use of tool 10 and thus membrane 65 has been removed from finger surface 63. Correspondingly, in the anticipated configuration of tool 10 for left handed use, membrane 55 has been left upon finger surface 63 of slide control button 61 (seen in FIG. 13) to provide complete closure of control aperture 52 leaving the instrument more responsive to control of suction using control aperture 62. It should be noted that the extension of end 31 of suction tube 30 provides maximum exposure of end 31 and generally corresponds to the use of tool 10 in an aspirating or suctioning mode. It should be recalled, however, that the extension of suction tube 30 with respect to electrocautery blade 20 is controlled by the position of slide control button 61 within slot 19 and as is set forth in FIGS. 6A through 6C is positionable at a plurality of detented positions.

FIG. 4 sets forth a top view of the present invention multifunction electrocautery tool. Tool 10 includes an elongated housing 11 defining an end 12 and an end 17. A suction tube 30 having a connecting end 33 is slidably supported within housing 11 and a blade receptacle 21 is secured to housing 11 and supports a removable electrocautery blade 20. Housing 11 defines side surfaces 15 and 16 and an upper surface 14. The latter supports a pair of switch buttons 40 and 41. A pair of slide control buttons 51 and 61 are slidably supported upon side surfaces 15 and 16 respectively. A connecting wire 23 extends through end 17 of housing 11 and is electrically coupled to blade receptacle 21 in the manner shown in FIG. 5.

FIG. 5 sets forth a section view of the present invention electrocautery tool taken along section lines 5—5 in FIG. 4. Tool 10 includes a housing 11 having an upper surface 14 and end portions 12 and 17. End portion 12 defines an aperture 83 while end portion 17 defines an aperture 84. An elongated cylindrical suction tube 30 having a connecting end 33 and a suction end 31 is received within housing 11 and extends outwardly through apertures 83 and 84. A plurality of guide members 80, 81 and 82 provide slidable supports for suction tube 30. Housing 11 further defines an upwardly extending detent lock 36, the structure of which is set forth below in FIGS. 6A through 6C in greater detail. However, suffice it to note here that detent lock 36 defines a detent recess 56 upon its upper surface. Correspondingly, suction tube 30 supports a plurality of outwardly extending detent ribs 37, 38 and 39 spaced upon suction tube 30 within its anticipated travel path within housing 11. As is described above, suction tube 30 further supports a slide control button 51 as well as an oppositely positioned slide control button 61 (seen in FIG. 3). Thus, suction tube 30 is slidably supported within housing 11 in response to movement of slide control button 51 and may be detentably positioned at three positions as detent ribs 37, 38 or 39 interact with detent lock 36 to provide a position detent and suction tube extension.

Housing 11 further defines an aperture 85 which receives a connecting wire 23. A blade receptacle 21 includes a blade socket 26 and is supported upon end 12 of housing 11 in accordance with conventional fabrication techniques. An electrical control circuit 70 constructed in accordance with conventional fabrication techniques includes a pair of depressible electric switches 42 and 43 positioned beneath a pair of depressible switch buttons 40 and 41 respectively. Control circuit 70 is constructed in accordance with conventional fabrication techniques and may, for example, include a conventional on/off connection capability as well as a high or low power capability utilizing for example a conventional resistive matrix. It will be apparent to those skilled in the art that virtually any control circuit may be utilized for control circuit 70 with the essential feature being the provision of control of the degree and coupling of electrical energy from connecting wire 23 to blade socket 26 via electrical connector 71.

In operation in the manner described above, the user is able to manipulate slide control button 51 to provide the desired extension of end 31 of suction tube 30. In addition, the cooperation of detent ribs 37 through 39 with detent lock 36 provides fixed position detenting at three positions corresponding to the alignment of each of detent ribs 37 through 39 with detent lock 36 in the manner described below in FIGS. 6A through 6C. It will be apparent, however, that in addition to the three detent positions provided for tool 11, suction tube 30 is otherwise freely slidable within housing 11 and thus is continuously positionable at a variety of slide positions between the retracted position shown in FIG. 5 and the extended position shown in FIG. 3. In addition to manipulating slide control button 51, the user is able to operate control circuit 70 by manipulation of switch buttons 40 and 41 to operate switches 42 and 43 respectively and thereby control the coupling of RF electrical energy to electrocautery blade 20.

FIGS. 6A through 6C set forth sequential section views illustrating the detent positioning of suction tube 30 within the present invention electrocautery tool.

More specifically, FIG. 6A sets forth a partial section view showing suction tube 30 supporting detent rib 37 movable within housing 11. In the position shown in FIG. 6A, suction tube 30 is moving in the direction indicated by arrow 57 such that detent rib 37 is moving toward detent lock 36 formed in housing 11. Suction tube 30 is otherwise freely movable within housing 11 in the manner described above to provide continuous positioning thereof. However, as detent rib 37 is brought into contact with detent lock 36 as suction tube moves in the direction of arrow 57, detent rib 37 is forced against the left edge of detent lock 36 in a somewhat interfering manner. The resiliency of suction tube 30 and housing 11 permits suction tube 30 to be moved farther in the direction indicated by arrow 57 forcing detent rib 37 into detent recess 56 of detent lock 36 and into the detented position shown in FIG. 6B.

As is seen in FIG. 6B, detent rib 37 is received within detent recess 56 of detent lock 36 producing a snap-fit type detenting action which tends to maintain the position of suction tube 30. This position corresponds to the alignment of detent rib 37 with detent recess 56.

FIG. 6C sets forth the position of suction tube 30 as it is moved beyond detent lock 36 in the direction indicated by arrow 57. As can be seen, detent rib 37 has, as a result, been forced out of detent recess 56 of lock 36 once again returning suction tube 30 to a freely movable or continuously movable position.

Figure 7:
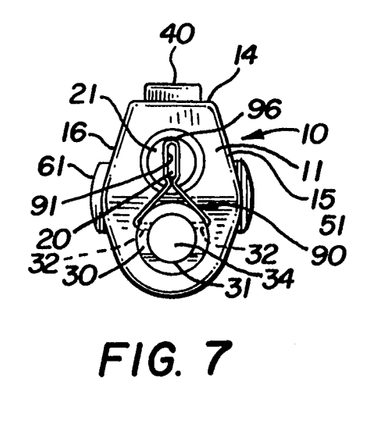
FIGS. 7 sets forth a front view of the present invention multifunction electrocautery tool.

FIG. 7 sets forth a front view of electrocautery tool 10 having blade cleaning accessory 90 supported upon suction tube 30 in accordance with a further advantage of the present invention structure. As described above, tool 10 includes a housing 11 having side surfaces 15 and 16 and an upper surface 14. A switch button 40 is supported upon upper surface 14 and a blade receptacle 21 supporting an electrocautery blade 20 extends forwardly from housing 11. A pair of slide control buttons 51 and 61 are slidably supported upon housing 11 and a generally cylindrical suction tube 30 having an interior passage 34 is slidably supported within housing 11 in the manner described above. In accordance with the present invention, slide control buttons 51 and 61 define respective control apertures 52 and 62 (seen in FIG. 13) which are coupled to interior passage 34 of suction tube 30 by a fitting 45 (also shown in FIG. 13). End 31 of suction tube 30 defines a plurality of apertures 32 extending through the sidewall of suction tube 30. A blade cleaning accessory 90 preferably formed of a spring material or the like is shown in detail in FIG. 9. However, suffice it to note here that blade cleaning accessory 90 defines a blade passage 91 through which blade 20 extends and a plurality of inwardly extending tabs 92 through 95 which are received within apertures 32 of suction tube 30. As mentioned, blade cleaning accessory 90 is preferably formed of a spring metal material and thus defines a spring bend 96 which resiliently maintains the position and configuration of blade cleaning accessory 90 and which resists outward spreading of tabs 92 through 95. Thus, spring bend 96 provides an inward spring force upon suction tube 30 which maintains the attachment of accessory 90 to suction tube 30 by maintaining the engagement of tabs 92 through 95 with apertures 32 of suction tube 30.

Figure 8A:
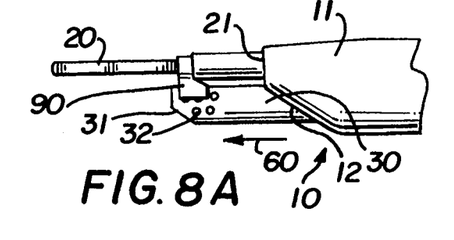
FIGS. 8A through 8C set forth partial sequential views of the electrocautery blade cleaning apparatus of the present invention electrocautery tool.

FIGS. 8A through 8C set forth sequential operation of the present invention blade cleaning accessory in response to movement of suction tube 30. FIG. 8A sets forth housing 11 having blade receptacle 21 supporting blade 20 and suction tube 30 having an end 31 and a plurality of apertures 32 positioned in the fully retracted position. A blade cleaning accessory 90 is received upon end 31 of suction tube 30 by the extension of a plurality of tabs 92 through 95 (seen in FIG. 9) into apertures 32. As described above, blade cleaning accessory 90 defines a blade passage 91 which receives blade 20.

Figure 8B:
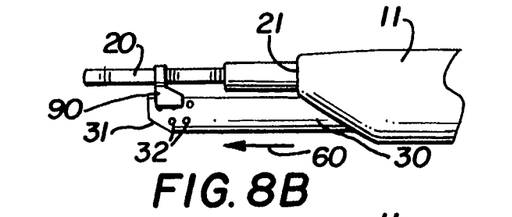
Figure 8C:
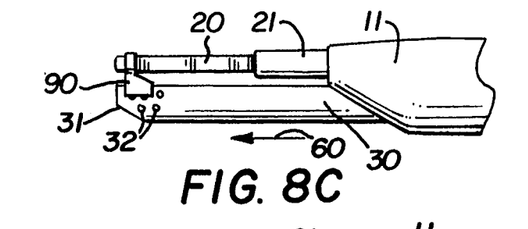

The cleaning operation is initiated by the user moving suction tube 30 forwardly in the direction indicated by arrow 60 through the manipulation of either slide control button 51 or 61. As suction tube 30 moves forwardly in the direction indicated by arrow 60, blade cleaning accessory 90 is moved correspondingly upon blade 20 as is sequentially shown in FIGS. 8B and 8C. FIGS. 8B shows an intermediate position of suction tube 30 and blade cleaning accessory 90 while FIG. 8C shows a maximally extended position of suction tube 30 and blade cleaning accessory 90. As blade cleaning accessory 90 slides forwardly upon blade 20, the close fit between blade 20 and blade passage 91 scrapes excess material and contamination from the side surfaces of blade 20 providing a cleaning action. Once suction tube 30 has reached a position shown in FIG. 8C, a reverse motion of suction tube 30 returns suction tube 30 to the retracted position shown in FIG. 8A and moves blade cleaning accessory upon blade 20 correspondingly. To maximize cleaning action, the user may undertake repeated motion of suction tube 30 and blade cleaning accessory 90 back and forth upon blade 20 essentially sequencing through the positions shown in FIGS. 8A through 8C.

Figure 9:
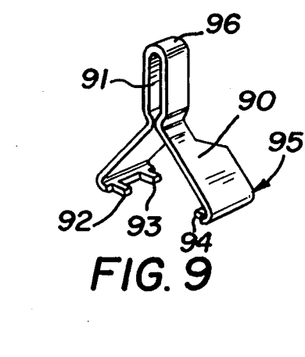
FIG. 9 sets forth a perspective view of the blade cleaning attachment of the present invention multifunction electrocautery tool.

FIG. 9 sets forth a perspective of blade cleaning accessory 90 having a blade passage 91 and a spring bend 96 formed therein. A plurality of tabs 92 through 95 extend inwardly from the lower portion of blade cleaning accessory 90 to engage apertures 32 of suction tube 30. As mentioned above, blade cleaning accessory 90 is preferably fabricated of a resilient or spring-type metal material such that spring bend 96 resists expansion of accessory 90 in a resilient fashion. This latter property facilitates the attachment of blade cleaning accessory 90 to suction tube 30 by temporarily spreading tabs 92 and 93 outwardly from tabs 93 and 94 and aligning them with apertures 32 to engage the apertures upon release.

Figures 10A, 10B:
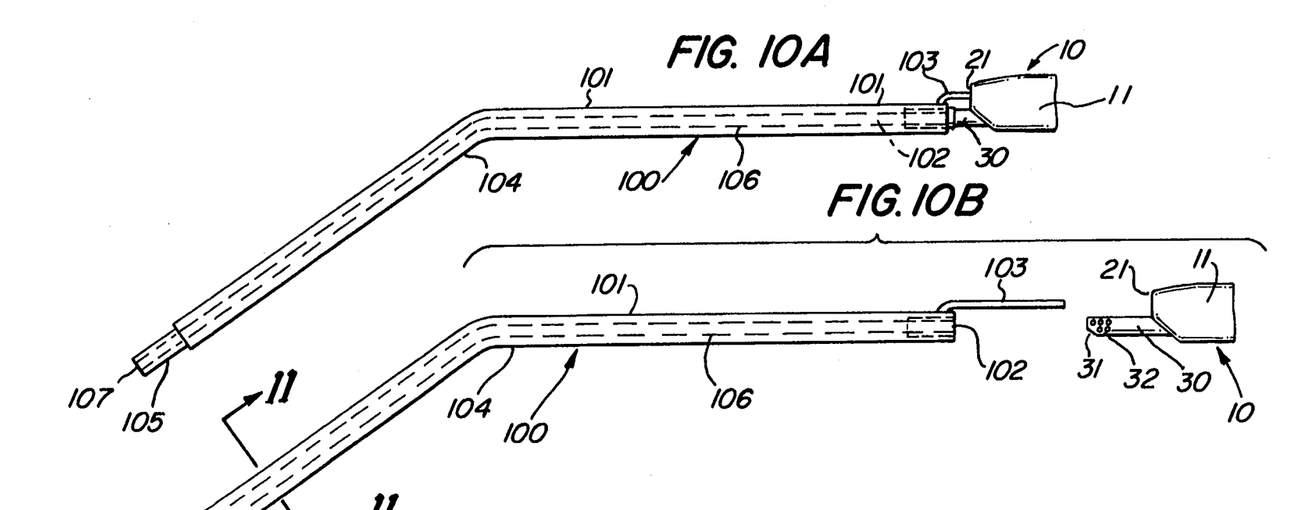
FIGS. 10A and 10B set forth assembly views of an attachable extender tube used in combination with the present invention multifunction electrocautery tool.

FIGS. 10A and 10B set forth a combination cauterizing and aspirating unit generally referenced by numeral 100. Extension 100 includes an elongated generally cylindrical probe 101 formed of an electrical conductive wall 106 having an interior passage 102 formed therein and an insulation sleeve 104 secured to the outer surface thereof. A connecting pin 103 is electrically coupled to conductive wall 106 and an open suction end 107 is surrounded by an exposed end portion 105 of conductive wall 106. In the position shown in FIG. 10A, extension unit 100 is assembled to electrocautery tool 10 such that interior passage 102 receives end portion 31 of suction tube 30 while connecting pin 103 is received within blade receptacle 21 supported within housing 11. With extension unit 100 thus installed in tool 10, a suction coupling is provided between suction tube 30 and probe 101 to produce a corresponding aspirating or suctioning action at end 107 of probe 101. In addition, the electrical connection between conductive wall 106 and blade receptacle 21 couples the above-mentioned RF electrical energy to conductive wall 106. Of particular interest is the coupling of electrical energy to exposed end 105 of probe 101. In accordance with the present invention, the coupling of suction tube 30 to probe 101 provides suctioning or aspirating action while the coupling of RF electrical energy to exposed end 105 of probe 101 provides a cauterizing action. As a result, the present invention extension used in combination with the present invention electrocautery tool facilitates the cauterizing and aspirating activities within deep wound sites and greatly enhances many surgical procedures. The use of insulation sleeve 104 upon conductive wall 106 prevents inadvertent cauterizing or burning of intermediate tissue in and about the deep wound site.

FIG. 10B sets forth extension unit 100 removed from electrocautery tool 10. Thus, comparison of FIGS. 10A and 10B illustrate the attachment and removal of extension unit 100. As can be seen, the attachment and removal of extension unit 100 is rendered easy and convenient due to the plug-in capability provided by interior passage 102 and connecting pin 103.

Figure 11:
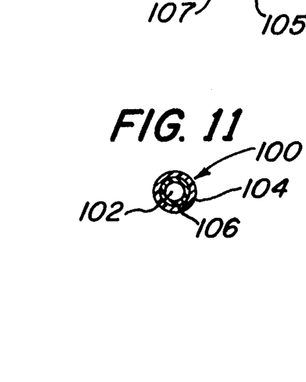
FIG. 11 sets forth a section view of the extender tube shown in FIG. 10B taken along section lines 11—11 therein.

FIG. 11 sets forth a section view of extension unit 100 taken along section lines 11—11 in FIG. 10B. As can be seen, probe 101 is preferably fabricated in a generally circular cross-section having a hollow circular cross-section wall 106 defining an interior passage 102 extending therethrough. Insulation sleeve 104 encircles conductive wall 106 providing an encircling and surrounding insulation sleeve to provide the above-described protection against inadvertent damage to tissue surrounding the surgical site or wound.

Figure 12:
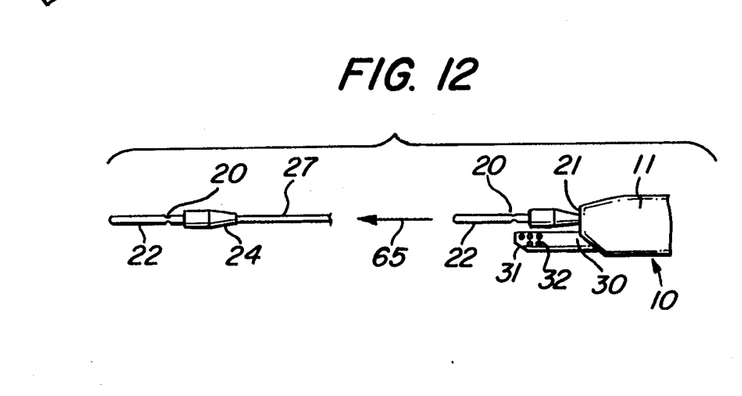
FIG. 12 sets forth a side elevation view of the attachment and removal of the cutting and cauterizing blade of the present invention multifunction electrocautery tool.

FIG. 12 sets forth the removal and assembly of cauterizing blade 20. As described above, tool 10 includes a housing 11 supporting suction tube 30 such that end 31 thereof extends forwardly. As is also described above, housing 11 supports a blade receptacle 21 within which electrocautery blade 20 is received. As is seen in FIG. 12 showing blade 20 removed by drawing blade 20 outwardly in the direction indicated by arrow 65, blade 20 includes an insulative collar 24 near its midpoint, a cutting edge 22 at one end and a connecting pin 27 at the remaining end. Connecting pin 27 is received within receptacle 21 in the manner shown in FIG. 5 to provide electrical connection to blade 20. In its preferred form, collar 24 simply surrounds a portion of pin 27 permitting pin 27 to extend through collar 24 in a continuous manner integral with the cutting portion of blade 20.

FIG. 13 sets forth a perspective assembly view of aspiration control 50 coupled to suction tube 30. As mentioned above, suction tube 30 defines an interior passage extending entirely through suction tube 30 and receives a fitting 45. Fitting 45 defines an axial portion 46 conforming generally to the outer surface of suction tube 30 and an elongated transversely oriented lateral portion 47. Lateral portion 47 defines a passage 48 extending therethrough which in accordance with the present invention is coupled to and communicates with interior passage 34 of suction tube 30. Thus, vacuum within suction tube 30 is coupled to passage 48 in an unobstructed coupling.

A pair of slide control buttons 51 and 61 define generally planar finger surfaces 53 and 63 respectively and inwardly extending boss portions 54 and 64 respectively. Bosses 54 and 64 are configured to be received within passage 48 on opposite end of fitting 45 to secure slide control buttons 51 and 61 to fitting 45. It should be recalled that fitting 45 is supported within the interior of housing 11 while slide control buttons 51 and 61 are supported on the outside of housing 11 extending through slots 18 and 19 (seen in FIGS. 1 and 3 respectively). Slide control button 51 and 61 define respective control apertures 52 and 62 which in the manner described above provide vacuum coupling to the interior of suction tube 30. To facilitate the use of the present invention electrocautery tool for both left-handed and right-handed persons, a pair of sealing membranes 55 and 65 are secured to finger surfaces 53 and 63 of slide control button 51 and 61 respectively. With both sealing membranes in place, the present invention tool may be readily configured for right hand or left hand use by simply removing the appropriate one of membrane 55 and 65. Preferably, membrane 55 is removed to provide right hand use while membrane 65 is removed to facilitate left hand use.

In its preferred form, suction tube 30 and fitting 45 may be integrally fabricated as a single molded plastic unit or the like to improve the economical manufacture of the present invention electrocautery tool. Slide control buttons 51 and 61 may be assembled to fitting 45 using a snap-fit attachment or, alternatively, bonding mechanisms such as adhesive bonding or sonic welding or other procedures may be utilized to secure the slide control buttons in place. Similarly, seal membranes 55 and 65 may be secured to finger surfaces 53 and 63 using conventional peel-off adhesives or mechanical attachment in accordance with the needs of the user.

It will be apparent to those skilled in the art that the present invention electrocautery tool set forth in FIGS. 1 through 13 provide substantial operative advantage over prior attempts to provide a multifunction electrocautery tool. The present invention provides both blade cleaning capability as well as the complete control of suction tube extension, cutting and cauterizing action, and aspirating using a single hand control without unduly encumbering the user's manipulation of the electrocautery tool. The easy control of aspirating or suctioning action through simple placement or removal of the user's thumb upon the control aperture of the slide control together with the use of that same slide control for manipulating the suction tube extension greatly improves the ease with which the present invention tool may be utilized. The accommodation of a convenient extension unit which provides both suction and cauterization further improves the utility and advantage of the present invention tool. Finally, the provision of detent apparatus operative upon the suction tube to maintain the suction tube fixed at a selected detent position from a plurality of detent positions further enhances the easy use of the present invention tool.

FIGS. 14 through 19 set forth an alternate embodiment of the present invention multifunction electrocautery tool utilizing an external electrical control for energizing and controlling the energizing of the electrocautery blade.

Figures 14, 15, 16, 17, 18, 19:
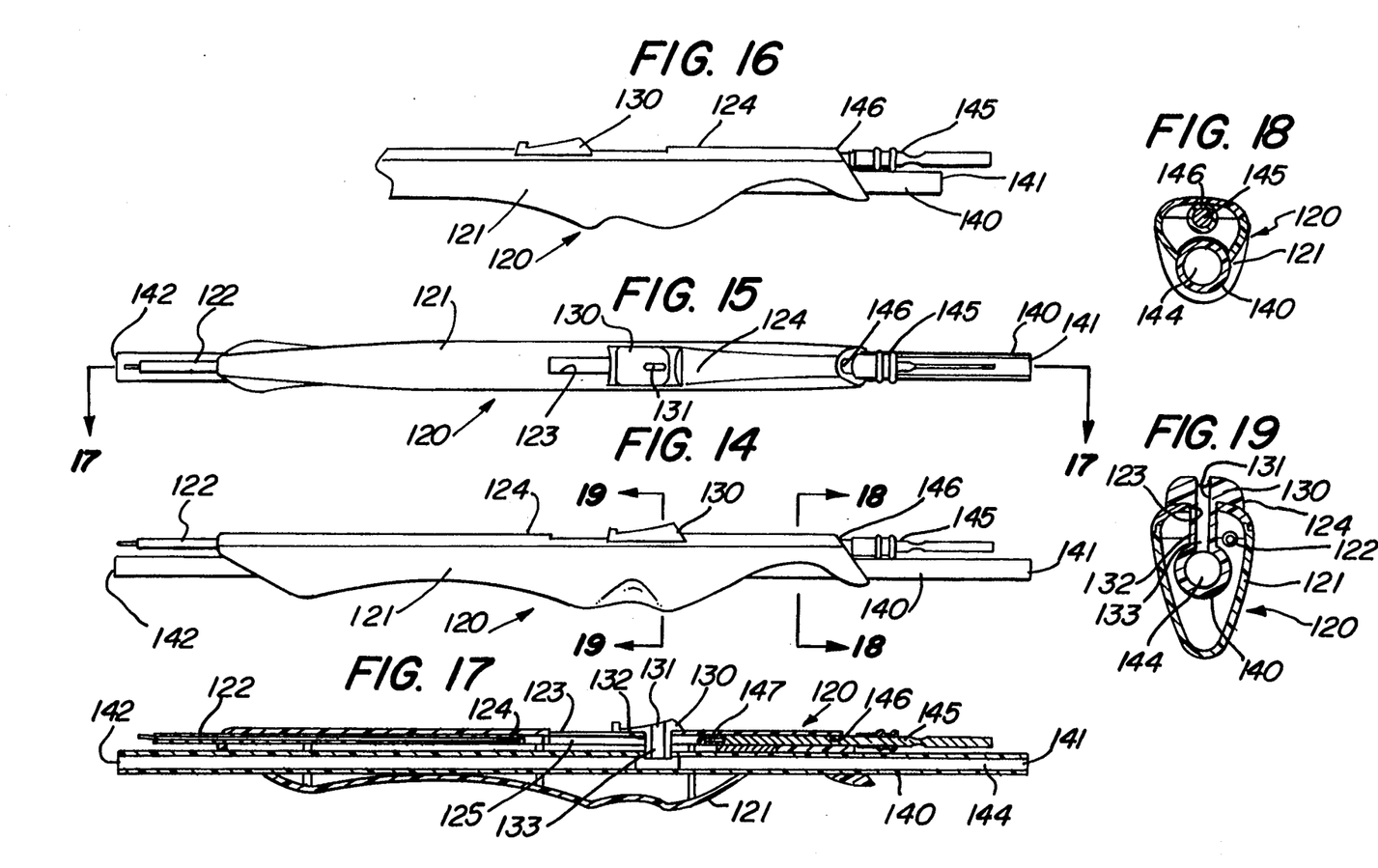
FIG. 14 sets forth a side elevation view of an alternate embodiment of the present invention multifunction electrocautery tool.
FIG. 15 sets forth a top view of the embodiment of the multifunction electrocautery tool of FIG. 14.
FIG. 16 sets forth a partial side elevation view of the embodiment of the present invention multifunction electrocautery tool of FIG. 14 having the suction tube in the retracted position.
FIG. 17 sets forth a section view of the alternate embodiment of the present invention multifunction electrocautery tool of FIG. 15 taken along section lines 17—17 therein.
FIG. 18 sets forth a section view of the alternate embodiment of the present invention multifunction electrocautery tool of FIG. 14 taken along section lines 18—18 therein.
FIG. 19 sets forth a section view of the alternate embodiment of the present invention multifunction electrocautery tool of FIG. 14 taken along section lines 19—19 therein.

FIG. 14 sets forth a side view of an alternate embodiment of the present invention multifunction electrocautery tool generally referenced by numeral 120. Tool 120 includes a housing 121 configured to conveniently sit within a user's hand and defining an upper surface 124 and an elongated slot 123 (seen in FIG. 15). As is better seen in FIG. 17, an elongated cylindrical suction tube 140 having an end 141 and a end 142 is slidably supported within housing 121. A slide control 130 is slidably supported upon upper surface 124 in the manner shown in FIG. 19. Tool 120 further includes a blade receptacle 146 which receives a blade 145 in much the same manner as set forth above for blade receptacle 21 and blade 20 of tool 10. In accordance with the present invention, suction tube 140 is slidably supported within housing 121 and is mechanically coupled to slide control 130. Thus, as the user moves slide control 130 upon upper surface 124, suction tube 140 is moved within housing 121 between the extended position shown in FIG. 14 and the retracted position shown in FIG. 16. As is better seen in FIG. 15, slide control 130 defines a control aperture 131 on the upper surface thereof. As is better seen in FIG. 19, suction tube 140 defines an interior passage 144 which is coupled to control aperture 131 by a coupler 132 having a passage 133 therebetween. Thus, in accordance with the present invention, the user is able to grasp tool 120 and place a finger or thumb upon the upper surface of slide control 130 to manipulate the extension of suction tube 140. In further accordance with the present invention, the same finger or thumb placement upon the upper surface of slide control 130 may be utilized by the user's to control the amount of suction within suction tube 140 by alternatively exposing or covering control aperture 131. An intermediate range of suction actions may be obtained by partial covering of control aperture 131. A connecting wire 122 couples blade 145 and blade receptacle 146 to a conventional source of RF electrical energy (not shown).

Thus, in accordance with the present invention, a single operative slide control 130 is operated by the user to provide simultaneous extension and retraction of suction tube 140 while controlling the degree of vacuum suction in operation without resorting to additional control elements. In the demanding surgical environment in which tools such as tool 120 are utilized, the ability to easily control the position of the suction tube as well as the degree of suctioning action using a single finger or thumb provides substantial operating advantage to the user.

FIG. 15 sets forth a top view of tool 120 showing housing 121 having blade receptacle 146 receiving and supporting blade 145 while suction tube 140 extends through housing 121 having ends 141 and 142 on either side thereof. FIG. 15 further shows upper surface 124 of housing 121 defining an elongated slot 123 which receives slide control 130 having control aperture 131 formed therein. A connecting wire 122 passes through housing 121 to provide electrical connection to blade 145.

FIG. 16 sets forth a partial view of tool 120 showing suction tube 140 in the retracted position. It should be noted that the retraction of suction tube 140 is achieved by sliding slide control 130 to the rearwardmost position as shown in FIG. 16.

FIG. 17 sets forth a section view of tool 120 taken along section lines 17—17 in FIG. 15. Housing 121 supports cylindrical suction tube 140 having end portions 141 and 142 and a center passage 144 formed therein. Housing 121 further defines a slot 123 upon upper surface 124 thereof within which a slide control 130 is movable. Slide control 130 defines a downwardly extending coupler 132 having a passage 133 formed therein and an upper control aperture 131. Aperture 131 communicates with interior passage 144 of suction tube 140 through passage 133. Mechanical coupling between slide control 130 and suction tube 140 is provided by coupler 132. A connecting wire 122 passes through housing 121 and includes a curved portion 125 which curves about slot 132 to avoid contact with coupler 133 and provides electrical connection to connector 147 of blade receptacle 146.

FIG. 18 sets forth a section view of tool 120 taken along section lines 18—18 in FIG. 14. As described above, tool 120 includes a housing 121 supporting a cylindrical suction tube 140 having an interior passage 144 formed therein. Blade receptacle 146 is supported within housing 121 and receives blade 145 in a removable attachment which provides electrical connection therebetween.

FIG. 19 sets forth a section view of tool 120 taken along section lines 19—19 in FIG. 14. As described above, tool 120 includes a housing 121 within which suction tube 140 is supported. Suction tube 140 defines an interior passage 144. Housing 121 defines an elongated slot 123 which receives a downwardly extending coupler 132 of slide control 130. Coupler 132 defines an interior passage 133 communicating with interior passage 144 of suction tube 140. Slide control 130 defines an aperture 131 in the upper surface thereof. Of particular note in FIG. 19 is the offset position of connecting wire 122 provided by curved portion 124 thereof shown in FIG. 17. The offset position of connecting wire 122 avoids interference between connecting wire 122 and coupler 132 thereby facilitating easy movement of slide control 130.

The embodiment of the present invention set forth in FIGS. 14 through 19 provides substantial advantage over prior art devices in that a single slide control is operative to simultaneously control the extension or retraction of the suction tube while also providing direct control of the degree of suctioning action through the user's covering or exposing of the control aperture formed therein. It is anticipated in the embodiment shown in FIGS. 14 through 19 than an external control mechanism will be utilized to control the RF electrical energy applied to the cauterizing blade.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention.

That which is claimed is:

1. A multifunction electrocautery tool comprising:
    an elongated housing;
    an elongated suction tube slidably supported within said housing and defining a suction passage therethrough;
    a slide control coupled to said suction tube and movably supported upon said housing, said slide control defining a control aperture and a control passage coupling said aperture to said interior passage of said suction tube; and
    an electrocautery blade supported upon said housing, said slide control being operable to move said suction tube within said housing and said control aperture being used to alter the suction characteristic of said suction tube, whereby said multifunction electrocautery tool provides combined control of the deployment of suction, tube retraction and aspiration control in a common unit operable in one hand.

2. A multifunction electrocautery tool as set forth in claim 1 wherein said slide control includes a pair of slide control buttons each having a control aperture formed therein and at least one seal membrane secured to at least one of said slide control buttons and covering the control aperture thereof.

3. A multifunction electrocautery tool as set forth in claim 2 wherein said housing defines opposed side surfaces and an upper surface and wherein said pair of slide control buttons are supported on each of said opposed side surfaces.

4. A multifunction electrocautery tool as set forth in claim 3 wherein each of said slide control buttons defines a generally planar finger surface surrounding each of said control apertures therein.

5. A multifunction electrocautery tool as set forth in claim 4 wherein said housing defines an elongated slot formed in each of said side surfaces and wherein said slide control includes a fitting received upon said suction tube and having a lateral portion generally extending between said slots and wherein said slide control buttons are secured to said lateral portion and extend through said slots.

6. A multifunction electrocautery tool as set forth in claim 5 further including at least one switch button supported upon said upper surface.

7. A multifunction electrocautery tool as set forth in claim 6 further including at least one switch supported within said housing coupled to said at least one switch button and a control circuit coupled to said switch and said electrocautery blade.

8. A multifunction electrocautery tool as set forth in claim 7 wherein said suction tube defines a connecting end most distant from said electrocautery blade and a suction end most proximate to said electrocautery blade and wherein said suction end moves generally parallel to said electrocautery blade as said slide control is moved.

9. A multifunction electrocautery tool as set forth in claim 8 further including a blade cleaning accessory having a cleaning passage for receiving said electrocautery blade and means for removably securing said accessory to said suction end.

10. A multifunction electrocautery tool as set forth in claim 9 wherein said means for removably securing includes a plurality of inwardly extending tabs formed on said accessory and wherein said suction tube defines a plurality of apertures proximate said suction end for receiving said tabs to secure said accessory.

11. A multifunction electrocautery tool as set forth in claim 10 wherein said housing includes a blade receptacle for removably receiving said electrocautery blade.

12. A multifunction electrocautery tool as set forth in claim 11 further including an extension unit having:
    an elongated hollow conductive probe having first and second ends and a cylindrical wall therebetween;
    an insulating sleeve upon said probe covering said first end and said cylindrical wall while leaving said second end exposed; and
    a connecting pin secured to said first end and extending generally beyond said first end, said extension unit being removably attachable to said housing by inserting said suction end of said suction tube into said first end and by inserting said connecting pin into said blade receptacle.

13. A multifunction electrocautery tool as set forth in claim 12 further including detent means for detentably positioning said suction tube in at least one position within said housing.

14. A multifunction electrocautery tool as set forth in claim 13 wherein said detent means includes:
   a plurality of ribs formed on said suction tube; and
   a detent lock formed within said housing and extending toward said ribs and engageable therewith.

15. A multifunction electrocautery tool as set forth in claim 1 wherein said suction tube defines a connecting end most distant from said electrocautery blade and a suction end most proximate to said electrocautery blade and wherein said suction end moves generally parallel to said electrocautery blade as said slide control is moved.

16. A multifunction electrocautery tool as set forth in claim 15 further including a blade cleaning accessory having a cleaning passage for receiving said electrocautery blade and means for removably securing said accessory to said suction end.

17. A multifunction electrocautery tool as set forth in claim 16 wherein said means for removably securing includes a plurality of inwardly extending tabs formed on said accessory and wherein said suction tube defines a plurality of apertures proximate said suction end for receiving said tabs to secure said accessory.

18. A multifunction electrocautery tool as set forth in claim 1 wherein said housing includes a blade receptacle for removably receiving said electrocautery blade.

19. A multifunction electrocautery tool as set forth in claim 18 further including an extension unit having:
   an elongated hollow conductive probe having first and second ends and a cylindrical wall therebetween;
   an insulating sleeve upon said probe covering said first end and said cylindrical wall while leaving said second end exposed; and
   a connecting pin secured to said first end and extending generally beyond said first end,
   said extension unit being removably attachable to said housing by inserting said suction end of said suction tube into said first end and by inserting said connecting pin into said blade receptacle.

20. A multifunction electrocautery tool as set forth in claim 1 further including detent means for detentably positioning said suction tube in at least one position within said housing.

21. A multifunction electrocautery tool as set forth in claim 20 wherein said detent means includes:
   a plurality of ribs formed on said suction tube; and
   a detent lock formed within said housing and extending toward said ribs and engageable therewith, 22. A multifunction electrocautery tool comprising:
   a hollow housing;
   a hollow suction tube defining a suction passage therethrough;
   means for slidably supporting said suction tube within said housing;
   a slide control button defining an outer surface and a control aperture therein;
   means for slidably supporting said slide control button upon said housing;
   a coupler coupled between said slide control button and said suction tube defining a passage coupling said control aperture to said suction passage; and
   a cauterizing blade supported upon said housing.

* * * * *